United States Patent
Harewood

(10) Patent No.: US 10,034,747 B2
(45) Date of Patent: Jul. 31, 2018

(54) PROSTHETIC VALVE SYSTEM HAVING A DOCKING COMPONENT AND A PROSTHETIC VALVE COMPONENT

(71) Applicant: Medtronic Vascular, Inc., Santa Rosa, CA (US)

(72) Inventor: Frank Harewood, Ballybrit (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 125 days.

(21) Appl. No.: 14/837,194

(22) Filed: Aug. 27, 2015

(65) Prior Publication Data

US 2017/0056162 A1  Mar. 2, 2017

(51) Int. Cl.
*A61F 2/06* (2013.01)
*A61F 2/24* (2006.01)
*A61F 2/07* (2013.01)

(52) U.S. Cl.
CPC .......... *A61F 2/2409* (2013.01); *A61F 2/2412* (2013.01); *A61F 2/2418* (2013.01);
(Continued)

(58) Field of Classification Search
None
See application file for complete search history.

(56) References Cited

U.S. PATENT DOCUMENTS 3,574,865 A   4/1971  Hamaker
3,997,923 A  12/1976  Possis
(Continued)

FOREIGN PATENT DOCUMENTS

WO   WO2007081820    7/2007
WO   WO2007130537   11/2007
(Continued)

OTHER PUBLICATIONS

PCT/US2016/048880, The International Search Report and The Written Opinion of the International Searching Authority, dated Dec. 8, 2016, 1-14pgs.

(Continued)

*Primary Examiner* — Brian Dukert
(74) *Attorney, Agent, or Firm* — Medler Ferro Woodhouse & Mills PLLC

(57) ABSTRACT

A two-component valve prosthesis system includes a docking component and a prosthetic valve component that is configured to be delivered separately from the docking component. The docking component has a compressed configuration for percutaneous delivery within a vasculature and an expanded configuration for deployment within a native heart valve. The docking component includes a tubular skirt, a first annular scaffold attached to a first end of the tubular skirt and a second annular scaffold attached to a second end of the tubular skirt. The first and second annular scaffolds are independent from each other. An intermediate portion of the tubular skirt is unsupported such that neither of the first or second annular scaffolds surrounds the intermediate portion of the tubular skirt. The prosthetic valve component has a compressed configuration for percutaneous delivery within a vasculature and an expanded configuration for deployment within the intermediate portion of the docking component.

19 Claims, 11 Drawing Sheets

(52) U.S. Cl.
CPC ......... *A61F 2/07* (2013.01); *A61F 2220/0016* (2013.01); *A61F 2250/0063* (2013.01)

(56) References Cited

U.S. PATENT DOCUMENTS

| | | | |
|---|---|---|---|
| RE31,040 E | 9/1982 | Possis | |
| 4,506,394 A | 3/1985 | Bedard | |
| 4,705,516 A | 11/1987 | Barone et al. | |
| 4,790,843 A | 12/1988 | Carpentier et al. | |
| 5,032,128 A | 7/1991 | Alonso et al. | |
| 5,332,402 A | 7/1994 | Teitelbaum | |
| 5,370,685 A | 12/1994 | Stevens et al. | |
| 5,716,370 A | 2/1998 | Williamson, IV et al. | |
| 5,984,959 A | 11/1999 | Robertson et al. | |
| 6,074,418 A | 6/2000 | Buchanan et al. | |
| 6,106,550 A | 8/2000 | Magovern et al. | |
| 6,176,877 B1 | 1/2001 | Buchanan et al. | |
| 6,217,611 B1 | 4/2001 | Klostermeyer | |
| 6,419,696 B1 | 7/2002 | Ortiz et al. | |
| 6,425,916 B1 | 7/2002 | Garrison et al. | |
| 6,468,305 B1 | 10/2002 | Otte | |
| 6,530,952 B2 | 3/2003 | Vesely | |
| 6,569,196 B1 | 5/2003 | Vesely | |
| 6,730,121 B2 | 5/2004 | Ortiz et al. | |
| 6,764,508 B1 | 7/2004 | Roehe et al. | |
| 6,786,925 B1 | 9/2004 | Schoon et al. | |
| 6,790,229 B1 | 9/2004 | Berreklouw | |
| 6,846,325 B2 | 1/2005 | Liddicoat | |
| 6,893,459 B1 | 5/2005 | Macoviak | |
| 6,908,481 B2 | 6/2005 | Cribier | |
| 6,939,365 B1 | 9/2005 | Fogarty et al. | |
| 6,964,684 B2 | 11/2005 | Ortiz et al. | |
| 7,011,681 B2 | 3/2006 | Vesely | |
| 7,097,659 B2 | 8/2006 | Woolfson et al. | |
| 7,147,663 B1 | 12/2006 | Berg et al. | |
| 7,172,625 B2 | 2/2007 | Shu et al. | |
| 7,186,265 B2 | 3/2007 | Sharkawy et al. | |
| 7,252,682 B2 | 8/2007 | Seguin | |
| 7,291,168 B2 | 11/2007 | Macoviak et al. | |
| 7,300,463 B2 | 11/2007 | Liddicoat | |
| 7,311,730 B2 | 12/2007 | Gabbay | |
| 7,381,220 B2 | 6/2008 | Macoviak et al. | |
| 7,503,930 B2 | 3/2009 | Sharkawy et al. | |
| 7,513,909 B2 | 4/2009 | Lane et al. | |
| 7,527,646 B2 | 5/2009 | Rahdert et al. | |
| 7,578,843 B2 | 8/2009 | Shu | |
| 7,585,321 B2 | 9/2009 | Cribier | |
| 7,597,711 B2 | 10/2009 | Drews et al. | |
| 7,611,535 B2 | 11/2009 | Woolfson et al. | |
| 7,648,528 B2 | 1/2010 | Styrc | |
| 7,691,144 B2 | 4/2010 | Chang et al. | |
| 7,708,775 B2 | 5/2010 | Rowe et al. | |
| 7,717,955 B2 | 5/2010 | Lane et al. | |
| 7,722,667 B1 | 5/2010 | Buchanan | |
| 7,758,640 B2 | 7/2010 | Vesely | |
| 7,771,469 B2 | 8/2010 | Liddicoat | |
| 7,776,083 B2 | 8/2010 | Vesely | |
| 7,846,203 B2 | 12/2010 | Cribier | |
| 7,846,204 B2 | 12/2010 | Letac et al. | |
| 7,887,583 B2 | 2/2011 | Macoviak | |
| 7,951,197 B2 | 5/2011 | Lane et al. | |
| 7,959,674 B2 | 6/2011 | Shu et al. | |
| 7,981,153 B2 | 7/2011 | Fogarty et al. | |
| 8,002,825 B2 | 8/2011 | Letac et al. | |
| 8,025,695 B2 | 9/2011 | Fogarty et al. | |
| 8,052,750 B2 | 11/2011 | Tuval et al. | |
| 8,057,540 B2 | 11/2011 | Letac et al. | |
| 8,070,800 B2 | 12/2011 | Lock et al. | |
| 8,083,793 B2 | 12/2011 | Lane et al. | |
| 8,105,377 B2 | 1/2012 | Liddicoat | |
| 8,142,496 B2 | 3/2012 | Berreklouw | |
| 8,163,013 B2 | 4/2012 | Machold et al. | |
| 8,187,207 B2 | 5/2012 | Machold et al. | |
| 8,236,049 B2 | 8/2012 | Rowe et al. | |
| 8,308,798 B2 | 11/2012 | Pintor et al. | |
| 8,323,335 B2 | 12/2012 | Rowe et al. | |
| 8,398,708 B2 | 3/2013 | Meiri et al. | |
| 8,474,460 B2 | 7/2013 | Barrett et al. | |
| 8,500,798 B2 * | 8/2013 | Rowe .................... A61F 2/2409 623/2.1 |
| 8,551,160 B2 | 10/2013 | Figulla et al. | |
| 8,551,161 B2 | 10/2013 | Dolan | |
| 8,591,573 B2 | 11/2013 | Barone | |
| 8,591,575 B2 | 11/2013 | Cribier | |
| 8,597,348 B2 | 12/2013 | Rowe et al. | |
| 8,657,872 B2 | 2/2014 | Seguin | |
| 8,685,086 B2 | 4/2014 | Navia et al. | |
| 8,771,345 B2 | 7/2014 | Tuval et al. | |
| 8,771,346 B2 | 7/2014 | Tuval et al. | |
| 8,834,561 B2 | 9/2014 | Figulla et al. | |
| 8,840,664 B2 | 9/2014 | Karapetian et al. | |
| 2001/0010017 A1 | 7/2001 | Letac et al. | |
| 2002/0032481 A1 | 3/2002 | Gabbay | |
| 2005/0137686 A1 | 6/2005 | Salahieh et al. | |
| 2005/0137691 A1 | 6/2005 | Salahieh et al. | |
| 2005/0203616 A1 | 9/2005 | Cribier | |
| 2006/0025855 A1* | 2/2006 | Lashinski .......... A61B 17/0644 623/2.1 |
| 2006/0195183 A1 | 8/2006 | Navia et al. | |
| 2007/0010876 A1 | 1/2007 | Salahieh et al. | |
| 2007/0016288 A1 | 1/2007 | Gurskis et al. | |
| 2008/0077234 A1 | 3/2008 | Styrc | |
| 2009/0281609 A1 | 11/2009 | Benichou et al. | |
| 2010/0036479 A1 | 2/2010 | Hill et al. | |
| 2010/0179649 A1 | 7/2010 | Richter et al. | |
| 2010/0249894 A1 | 9/2010 | Oba et al. | |
| 2010/0280606 A1 | 11/2010 | Naor | |
| 2010/0312333 A1 | 12/2010 | Navia et al. | |
| 2011/0160846 A1 | 6/2011 | Bishop et al. | |
| 2011/0224785 A1 | 9/2011 | Hacohen | |
| 2012/0022640 A1 | 1/2012 | Gross et al. | |
| 2012/0046741 A1 | 2/2012 | Tuval et al. | |
| 2012/0059458 A1 | 3/2012 | Buchbinder et al. | |
| 2012/0083839 A1 | 4/2012 | Letac et al. | |
| 2012/0101571 A1 | 4/2012 | Thambar et al. | |
| 2012/0323317 A1* | 12/2012 | Karapetian .......... A61F 2/2409 623/2.37 |
| 2013/0035759 A1 | 2/2013 | Gross et al. | |
| 2013/0166022 A1 | 6/2013 | Conklin | |
| 2013/0172992 A1 | 7/2013 | Gross et al. | |
| 2013/0190865 A1 | 7/2013 | Anderson | |
| 2013/0211491 A1 | 8/2013 | Berreklouw | |
| 2013/0245753 A1 | 9/2013 | Alkhatib | |
| 2013/0317598 A1 | 11/2013 | Rowe et al. | |
| 2014/0005778 A1 | 1/2014 | Buchbinder et al. | |
| 2014/0207231 A1 | 7/2014 | Hacohen et al. | |
| 2014/0214160 A1 | 7/2014 | Naor | |
| 2014/0249622 A1 | 9/2014 | Carmi et al. | |
| 2014/0309680 A1 | 10/2014 | Fargahi | |
| 2014/0309727 A1 | 10/2014 | Lamelas et al. | |
| 2014/0309730 A1 | 10/2014 | Alon et al. | |
| 2014/0324164 A1 | 10/2014 | Gross et al. | |
| 2014/0358222 A1 | 12/2014 | Gorman, III et al. | |

FOREIGN PATENT DOCUMENTS

| | | |
|---|---|---|
| WO | WO2014080339 | 5/2014 |
| WO | WO2014081796 | 5/2014 |
| WO | WO2015023579 | 2/2015 |

OTHER PUBLICATIONS

Examination Report dated May 22, 2018 in corresponding Australian Patent Application No. 2016312628.

* cited by examiner

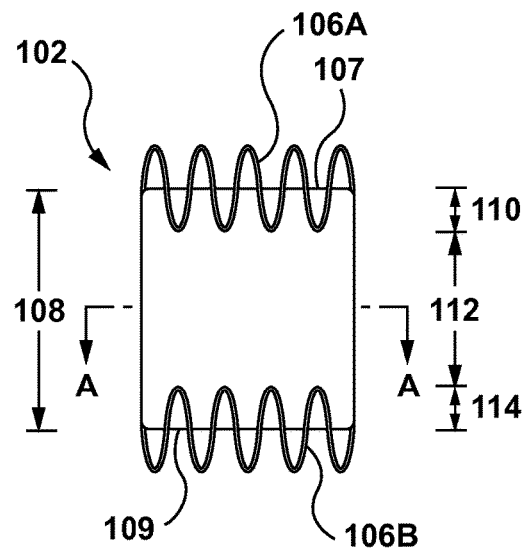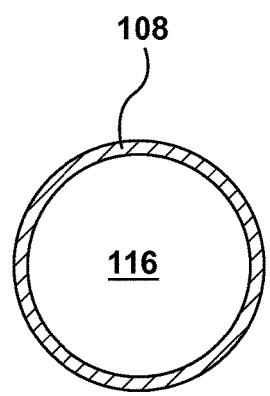
FIG. 3
FIG. 3A
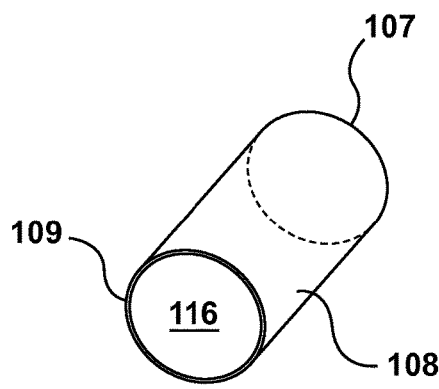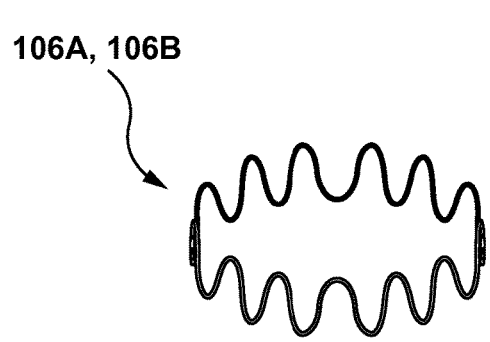
FIG. 4
FIG. 5

PROSTHETIC VALVE SYSTEM HAVING A DOCKING COMPONENT AND A PROSTHETIC VALVE COMPONENT

FIELD OF THE INVENTION

The invention relates in general to valve prostheses and more particularly to a valve prosthesis for transcatheter delivery.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis, in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent or scaffold structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by compressing onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Pat. No. 8,721,713, both filed by Tower et al., each of which is incorporated by reference herein in its entirety.

Although transcatheter delivery methods have provided safer and less invasive methods for replacing a defective native heart valve, complications may arise including vessel trauma due to percutaneous delivery within highly curved anatomy and/or due to a large delivery profile of the prosthesis, inaccurate placement of the valve prosthesis, conduction disturbances, coronary artery obstruction, and/or undesirable paravalvular leakage and/or regurgitation at the implantation site. Embodiments hereof are directed to a valve prosthesis system having an improved configuration to address one or more of the afore-mentioned complications.

BRIEF SUMMARY OF THE INVENTION

Embodiments hereof relate to a valve prosthesis system includes a docking component and a prosthetic valve component. The prosthetic valve component is configured to be delivered separately from the docking component. The docking component has a compressed configuration for percutaneous delivery within a vasculature and an expanded configuration for deployment within a native heart valve. The docking component includes a tubular body formed from an impermeable material, the tubular body having opposing first and second end portions and an intermediate portion extending between the first and second end portions, a first annular scaffold attached to the tubular body along the first end portion thereof, and a second annular scaffold attached to the tubular body along the second end portion thereof. The first and second annular scaffolds are independent from each other. The intermediate portion of the tubular body is unsupported such that neither of the first or second annular scaffolds surrounds the intermediate portion of the tubular body. The prosthetic valve component has a compressed configuration for percutaneous delivery within a vasculature and an expanded configuration for deployment within the intermediate portion of the docking component.

Embodiments hereof also relate to a valve prosthesis system includes an exterior docking component and an interior dockable component. The exterior docking component has a compressed configuration for percutaneous delivery within a vasculature and an expanded configuration for deployment within a native heart valve. The exterior docking component includes a tubular skirt, a first annular scaffold attached to a first end of the tubular skirt, and a second annular scaffold attached to a second end of the tubular skirt. The first and second annular scaffolds are independent from each other and an intermediate portion of the tubular skirt that longitudinally extends between the first and second annular scaffolds is unsupported such that neither of the first or second annular scaffolds surrounds the intermediate portion of the tubular skirt. The interior dockable component has a compressed configuration for percutaneous delivery within a vasculature and an expanded configuration for deployment within the skirt of the exterior docking component. The interior dockable component includes a scaffold and at least two valve leaflets disposed within and secured to the scaffold. The interior dockable component is configured to be delivered separately from the exterior docking component and the interior dockable component is configured to couple to the intermediate portion of the tubular skirt of the exterior docking component in situ such that the tubular skirt is radially disposed around and contacts the interior dockable component.

Embodiments hereof also relate to method of deploying a valve prosthesis system in situ. A docking component is percutaneously delivered within a vasculature to a native heart valve. The docking component is in a compressed configuration during delivery. The docking component includes a tubular body formed from an impermeable material, a first annular scaffold attached to the tubular body along a first end portion thereof, and a second annular scaffold attached to the tubular body along a second end portion thereof, the first and second annular scaffolds being independent from each other and an intermediate portion of the tubular body being unsupported such that neither of the first or second annular scaffolds surround the intermediate portion of the tubular body. The docking component is deployed to an expanded configuration within the native heart valve. A prosthetic valve component is percutaneously delivered within a vasculature to the native heart valve. The prosthetic valve component is in a compressed configuration during delivery. The prosthetic valve component is deployed to an expanded configuration within the intermediate portion of the docking component. Deployment of the prosthetic valve component occurs after deployment of the docking component.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3 is a side view of the docking component of FIG. 1, wherein the docking component is removed from the valve prosthesis system for illustrative purposes only.

FIG. 3A is a cross-sectional view taken along line A-A of FIG. 3.

FIG. 4 is a perspective view of a tubular skirt of the docking component of FIG. 3.

FIG. 5 is a side view of an annular scaffold of the docking component of FIG. 3.

DETAILED DESCRIPTION OF THE INVENTION

Figure 1:
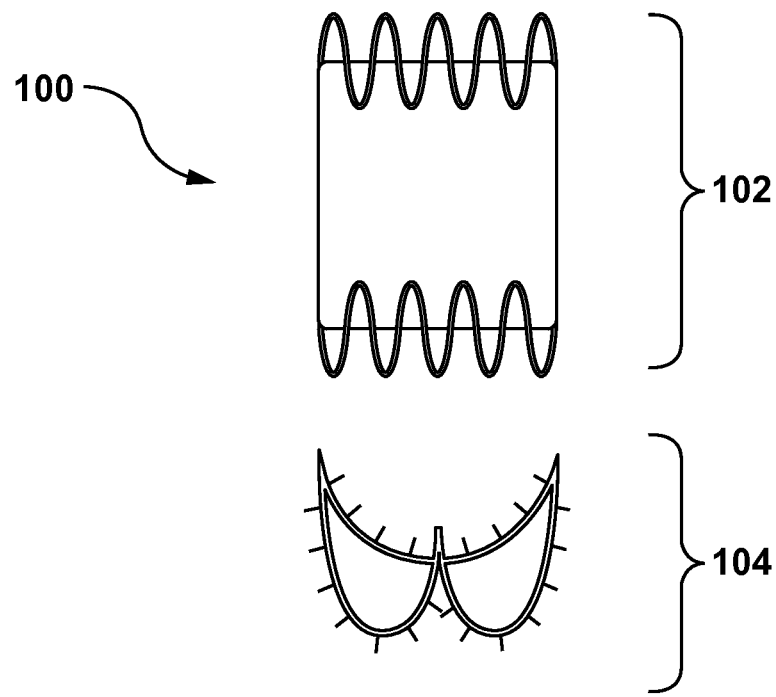
FIG. 1 is an exploded view of a valve prosthesis system according to an embodiment hereof, wherein the valve prosthesis system includes a docking component and a prosthetic valve component, the docking component and the prosthetic valve component each being shown in an expanded configuration.

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description with reference to one or more support structures of the valve prosthesis systems hereof and is intended to convey that the structures are shaped or formed from a material that can be provided with a mechanical memory to return the structure from a compressed or constricted delivery configuration to an expanded deployed configuration. Non-exhaustive exemplary self-expanding materials include a pseudo-elastic metal such as a nickel titanium alloy or nitinol, a spring-tempered steel, various polymers, or a so-called super alloy, which may have a base metal of nickel, cobalt, chromium, or other metal. Mechanical memory may be imparted to a wire or scaffold structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and polycyclooctene can be used separately or in conjunction with other shape memory polymers.

The following detailed description is merely exemplary in nature and is not intended to limit the invention or the application and uses of the invention. Although the description of the invention is in the context of replacement of aortic valves, the prosthetic valves of the invention can also be used in other areas of the body, such as for replacement of a native mitral valve, for replacement of a native pulmonic valve, for replacement of a native tricuspid valve, for use as a venous valve, or for replacement of a failed previously-implanted prosthesis. Furthermore, there is no intention to be bound by any expressed or implied theory presented in the preceding technical field, background, brief summary or the following detailed description.

Embodiments hereof relate to a two-component valve prosthesis system that includes a docking component and a prosthetic valve component. The prosthetic valve component is configured to be delivered and/or deployed separately from the docking component. The docking component includes two anchoring scaffold or stent-like structures at inflow and outflow ends thereof that are separated and connected by a tubular skirt. An unsupported or scaffold-free intermediate portion of the tubular skirt extends between the anchoring scaffolds of the docking component. In situ, the prosthetic valve component is deployed against the unsupported intermediate portion of the tubular skirt. The scaffold-free intermediate portion of the tubular skirt thus functions as a landing zone for deployment of the prosthetic valve component and also functions as a continuous circumferential seal around the deployed prosthetic valve component to block or prevent blood flow around the outer perimeter thereof thereby minimizing and/or eliminating any paravalvular leakage at the implantation site.

Figure 2:
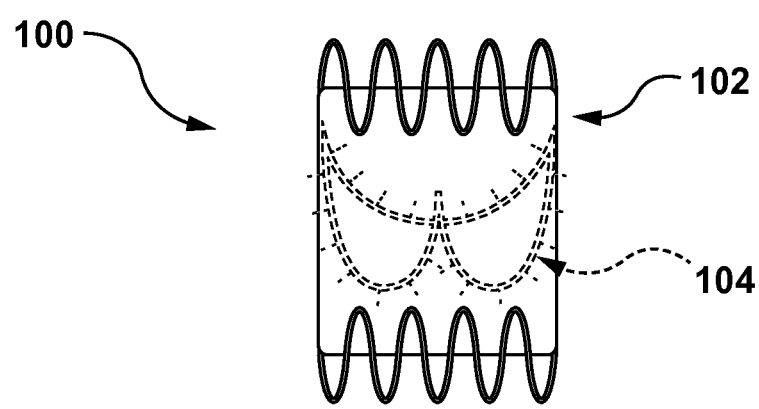
FIG. 2 is a side view of the valve prosthesis system of FIG. 1, wherein the prosthetic valve component is disposed within the docking component.

More particularly, FIG. 1 and FIG. 2 illustrate a valve prosthesis system 100 according to an embodiment hereof. Valve prosthesis system 100 includes a docking component 102 and a prosthetic valve component 104. FIG. 1 is an exploded side view in which docking component 102 and prosthetic valve component 104 are each shown separately in an expanded configuration, while FIG. 2 is a side view in which prosthetic valve component 104 is disposed within docking component 102. Docking component 102 is also referred to herein as an exterior docking component and prosthetic valve component 104 is also referred to herein as an interior dockable component. Docking component 102 is configured to fit and conform to the anatomy when expanded or deployed in situ in order to prevent paravalvular leakage (PVL) and prosthetic valve component 104 is implanted into docking component 102. As such, docking component 102 may be designed, sized, or otherwise configured to fit and conform to native heart anatomy at any desired valve location, while prosthetic valve component 104 has a universal or common optimized design that fits into any or all docking component(s). Accordingly, valve prosthesis system 100 is designed so that a single or universal prosthetic valve component 104 may be deployed at a multitude of heart valve sites (i.e., aortic, mitral, tricuspid, pulmonic).

Docking component 102 has a compressed configuration for percutaneous delivery within a vasculature and an expanded configuration for deployment within a native heart valve. FIG. 3 is a side view of docking component 102 in the expanded configuration, the docking component being removed from valve prosthesis system 100 for illustrative purposes only. FIG. 3A is a cross-sectional view taken along line A-A of FIG. 3. Docking component 102 includes a tubular body or skirt 108, a first annular scaffold 106A, and a second annular scaffold 106B. When configured as a replacement for an aortic valve, second annular scaffold 106B functions as an inflow end of valve prosthesis system 100 and anchors within the aortic annulus, while first annular scaffold 106A functions as an outflow end of valve prosthesis system 100 and anchors within the aortic annulus. "Inflow" and "outflow" refers to the direction of blood flow relative to the valve prosthesis system once it is implanted in a patient.

Tubular skirt 108 is constructed from an impermeable biocompatible material such as but not limited to a polymer material, a fabric material, or a pericardium that is shaped as a tubular body to define lumen 116 there-through as shown in the cross-sectional view of FIG. 3A. Lumen 116 is also illustrated in FIG. 4, which is a perspective view of tubular skirt 108 removed from docking component 102 for illustrative purposes only. Tubular skirt 108 has a first end 107 and a second or opposing end 109. Suitable materials include but are not limited to a low-porosity fabric, such as polyester, DACRON®, or polytetrafluoroethylene (PTFE). Tubular skirt 108 is thin-walled so that valve prosthesis system 100 may be compressed into a small diameter, yet is capable of acting as a strong, leak-resistant fluid conduit when expanded to a cylindrical tubular form. In one embodiment, tubular skirt 108 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment hereof, tubular skirt 108 may be made of pericardial material. Natural tissue for tubular skirt 108 may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals.

First annular scaffold 106A is attached to first end 107 of tubular skirt 108, and second annular scaffold 106B is attached to second or opposing end 109 of tubular skirt 108. As shown in FIG. 3, tubular skirt 108 includes a first end portion 110, a second or opposing end portion 114, and an intermediate portion 112 that extends between first and second end portions 110, 114. Intermediate portion 112 of tubular skirt 108 is unsupported or scaffold-free such that neither of first or second annular scaffolds 106A, 106B surround the intermediate portion of the tubular skirt as will be described in more detail herein. First annular scaffold 106A is attached to tubular skirt 108 along first end portion 110, and second annular scaffold 106B is attached to the tubular body along second end portion 114 thereof. Intermediate portion 112 of tubular skirt 108 longitudinally extends between first and second annular scaffolds 106A, 106B. The length of each portion, i.e., first end portion 110, intermediate portion 112, and second end portion 114, may vary depending on the desired application, on the desired native valve location for the prosthesis, and/or on the size of the patient.

First and second annular scaffolds 106A, 106B are stent-like structures that are independent of each other. "Independent" as used herein means that first and second annular scaffolds are separate from each other and are not directly attached to each other. However, first and second annular scaffolds 106A, 106B are connected or indirectly linked to each other via intermediate portion 112 of tubular skirt 108 that extends therebetween as described above.

Figure 6:
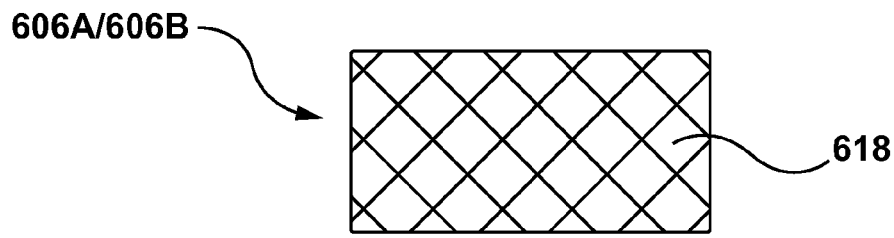
FIG. 6 is a side view of a tubular scaffold of a docking component according to another embodiment hereof, wherein the tubular scaffold is shown in an expanded configuration.

First and second annular scaffolds 106A, 106B are both self-expanding components that return to an expanded deployed state from a compressed or constricted delivery state. First and second annular scaffolds 106A, 106B are both sized to anchor valve prosthesis system 100 against native valve tissue when the prosthesis is in the expanded configuration. In this embodiment, first and second annular scaffolds 106A, 106B each include a sinusoidal patterned ring as shown in the perspective view of FIG. 5. However, it will be understood by one of ordinary skill in the art that the illustrated configurations of first and second annular scaffolds 106A, 106B are exemplary and first and second annular scaffolds 106A, 106B may have alternative patterns or configurations. For example, in another embodiment shown in FIG. 6, first and second annular scaffolds 606A, 606B are tubular components having diamond-shaped openings 618 which may be formed by a laser-cut manufacturing method and/or another conventional stent/scaffold forming method as would be understood by one of ordinary skill in the art. In another embodiment hereof (not shown), the first and second annular scaffolds may each have distinct configurations and/or include an additional element such as a flared end portion that aids in fixing or anchoring docking component 102 within native valve anatomy. Further, in another embodiment hereof, the first and second annular scaffolds are configured to be balloon-expandable rather than self-expanding and thus would not be required to be formed from a shape memory material.

First and second annular scaffolds 106A, 106B are coupled to first and second end portions 110, 114, respectively, of tubular skirt 108 in order to bias and/or anchor the first and second end portions of tubular skirt 108 into apposition with an interior wall of a body lumen (not shown). First and second end portions 110, 114, respectively, of tubular skirt 108 are thus supported by first and second annular scaffolds 106A, 106B. As used herein, "supported" means that the graft material of first and second end portions 110, 114 of tubular skirt 108 has radial support along its length and circumference. In particular, first annular scaffold 106A surrounds and overlaps with first end portion 110 of tubular skirt 108 and second annular scaffold 106B surrounds and overlaps with second end portion 114 of tubular fabric body. First and second annular scaffolds 106A, 106B may longitudinally extend up to or beyond first and second ends 107, 109, respectively, of tubular skirt 108. FIG. 1 illustrates an embodiment in which both first and second annular scaffolds 106A, 106B longitudinally extend beyond first and second ends 107, 109, respectively, of tubular skirt 108. Alternatively, in another embodiment (now shown), first annular scaffold 106A may longitudinally extend up to but not beyond first end 107 of tubular skirt 108 and/or second annular scaffold 106B may longitudinally extend up to but not beyond second end 109 of tubular skirt 108. First and second annular scaffolds 106A, 106B may be attached or mechanically coupled to first and second end portions 110, 114, respectively, of tubular skirt 108 by various means, such as, for example, by stitching or suturing onto either an inner surface or an outer surface of tubular skirt 108.

Intermediate portion 112 of tubular skirt 108 is scaffold-free and unsupported. "Unsupported" as used herein means that the material of intermediate portion 112 of tubular skirt 108 has no radial support along its length or circumference and is not surrounded by any tubular or annular scaffold or stent-like structure. Stated another way, first and second annular scaffolds 106A, 106B do not surround and do not overlap intermediate portion 112 of tubular skirt 108. Intermediate portion 112 of tubular skirt 108 provides a landing site or zone for prosthetic valve component 104, which is delivered separately from docking component 102 as described in more detail herein.

Figure 7:
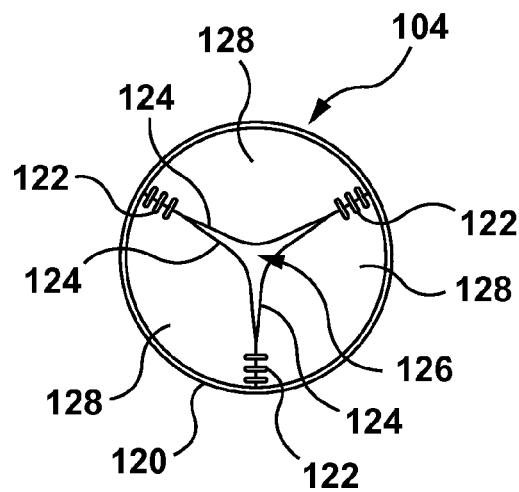
FIG. 7 is an end view of the prosthetic valve component of FIG. 1, taken from the second or outflow end thereof, wherein the prosthetic valve component is removed from the valve prosthesis system for illustrative purposes only.

Prosthetic valve component 104 has a compressed configuration for percutaneous delivery within a vasculature and an expanded configuration for deployment within the intermediate portion of the docking component. Prosthetic valve component 104 includes a scaffold 120 formed from a self-expanding material and at least two valve leaflets 128 disposed within and secured to scaffold 120. Prosthetic valve component 104 is capable of blocking flow in one direction to regulate flow there-through via valve leaflets 128 that may form a bicuspid or tricuspid replacement valve. FIG. 7 is an end view of prosthetic valve component 104 taken from the second or outflow end thereof, the prosthetic valve component being removed from valve prosthesis system 100 for illustrative purposes only. FIG. 7 illustrates an exemplary tricuspid valve having three leaflets 128, although a bicuspid leaflet configuration may alternatively be used in embodiments hereof. More particularly, if valve prosthesis system 100 is configured for placement within a native valve having three leaflets such as the aortic, tricuspid, or pulmonary valves, valve prosthesis system 100 includes three valve leaflets 128 although the valve prosthesis is not required to have the same number of leaflets as the native valve. If valve prosthesis system 100 is configured for placement within a native valve having two leaflets such as the mitral valve, valve prosthesis system 100 includes two or three valve leaflets 128. Valve leaflets 128 are sutured or otherwise securely and sealingly attached (i.e., via suitable biocompatible adhesive) to the inner surface of scaffold 120. Adjoining pairs of leaflets are attached to one another at their lateral ends to form commissures 122, with free edges 124 of the leaflets forming coaptation edges that meet in area of coaptation 126.

Leaflets 128 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 128 include DACRON® commercially available from Invista North America S.A.R.L. of Wilmington, Del., other cloth materials, nylon blends, and polymeric materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Figure 8:
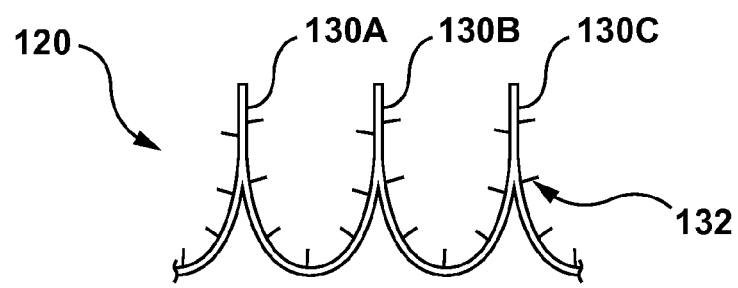
FIG. 8 is a side view of a scaffold of the prosthetic valve component of FIG. 7, wherein the scaffold is laid flat for illustrative purposes only.
Figure 10:
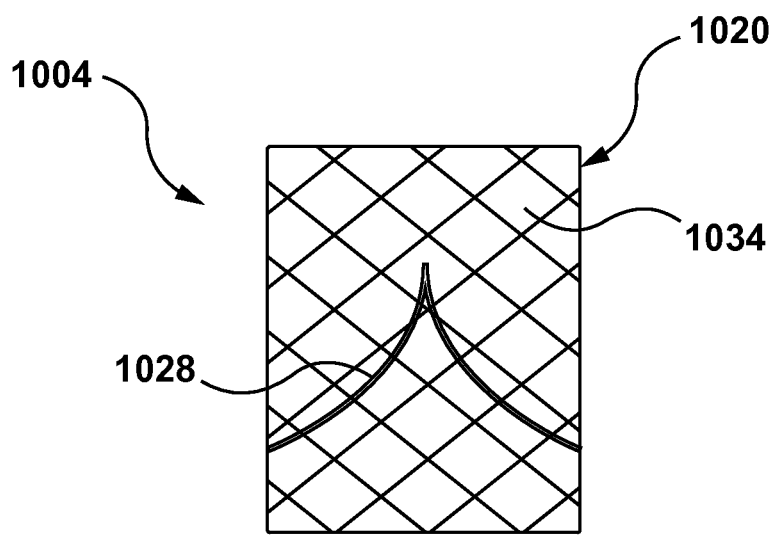
FIG. 10 is a side view of a prosthetic valve component according to another embodiment hereof, wherein prosthetic valve component includes a tubular scaffold and the tubular scaffold is shown in an expanded configuration.

FIG. 8 is a side view of scaffold 120 laid flat for illustrative purposes only. In this embodiment, scaffold 120 is an annular ring that defines three posts 130A, 130B, 130C aligned with commissures 122 of leaflets 128. Scaffold 120 is formed from a strand or wire-like element formed into an annular ring. However, it will be understood by one of ordinary skill in the art that the illustrated configurations of scaffold 120 is exemplary and scaffold 120 may have an alternative pattern or configuration. For example, in another embodiment shown in FIG. 10, a prosthetic valve component 1004 includes a plurality of leaflets 1028 disposed within a tubular scaffold 1020 formed from a self-expanding material, the tubular scaffold defining diamond-shaped openings 1034 which may be formed by a laser-cut manufacturing method and/or another conventional stent/scaffold forming method as would be understood by one of ordinary skill in the art. Further, in another embodiment hereof, the scaffold of the prosthetic valve component is configured to be balloon-expandable rather than self-expanding and thus would not be required to be formed from a shape memory material.

Prosthetic valve component 104 is configured to be delivered separately from docking component 102 and is configured to couple to intermediate portion 112 of tubular skirt 108 of docking component 102 in situ such that the tubular skirt is radially disposed around and contacts scaffold 120 of prosthetic valve component 104. As previously stated, intermediate portion 112 of tubular skirt 108 thus serves as a landing or target zone for deployment of prosthetic valve component 104. In addition, when tubular skirt 108 is radially disposed around prosthetic valve component 104 after deployment of the prosthetic valve component, tubular skirt 108 prevents paravalvular leakage (PVL) by functioning to occlude or fill gaps between the perimeter of prosthetic valve component 104 and the native valve annulus, thereby reducing, minimizing, or eliminating leaks therebetween. The native valve annulus may include surface irregularities on the inner surface thereof, and as a result one or more gaps or cavities/crevices may be present or may form between the perimeter of the valve prosthesis and the native valve annulus. For example, calcium deposits may be present on the native valve leaflets (e.g., stenotic valve leaflets) and/or shape differences may be present between the native heart annulus and the valve prosthesis. More particularly, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site. In embodiments hereof, tubular skirt 108 functions to block any retrograde flow within the native valve, thereby preventing undesired regurgitation and preventing blood stagnation in and around the native valve sinuses. In addition, tubular skirt 108 fills any/all gaps or cavities/crevices between the outer surface of scaffold 120 and native valve tissue such that blood flow through the target gap or cavity is occluded or blocked, or stated another way blood is not permitted to flow therethrough. Tubular skirt 108 functions as a continuous circumferential seal around prosthetic valve component 104 to block or prevent blood flow around the outer perimeter thereof, thereby minimizing and/or eliminating any paravalvular leakage at the implantation site.

In an embodiment hereof, prosthetic valve component 104 is approximately 10 mm in longitudinal length and a diameter (in the expanded configuration) will be sized to fit the native patient anatomy and to provide an interference fit with intermediate portion 112 of tubular skirt 108 of docking component 102. Intermediate portion 112 of tubular skirt 108 of docking component 102 has a longitudinal length at least as long as prosthetic valve component 104 to allow successful docking.

Figure 9:
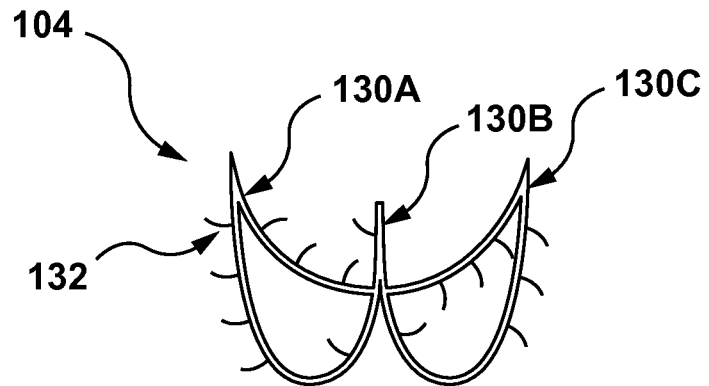
FIG. 9 is a perspective view of a scaffold of the prosthetic valve component of FIG. 1, wherein barbs of the scaffold are shown and the scaffold is shown in an expanded configuration.

As best shown in FIG. 9, scaffold 120 includes a plurality of barbs or hooks 132 on an outside surface thereof to aid in fixation thereof to docking component 102. Barbs 132 are configured to catch, grab, or otherwise embed into intermediate portion 112 of tubular skirt 108 of docking component 102 in order to couple prosthetic valve component 104 to docking component 102 in situ. Barbs 132 radially extend away from scaffold 120 and each barb includes a free end that is sharp enough to engage with intermediate portion 112 of tubular skirt 108. Barbs 132 extend at an acute angle relative to the outer surface of scaffold 120 so that they extend at least slightly outward relative to the outer surface of the scaffold. Barbs 132 may be coupled to scaffold 120 or integrally formed therewith. As explained in more detail herein, during implantation, prosthetic valve component 104 is partially deployed into docking component 102 and then rotated in order to embed barbs 132 into intermediate portion 112 of tubular skirt 108. After barbs 132 are embedded as desired, prosthetic valve component 104 is fully deployed into docking component 102.

Figure 11:
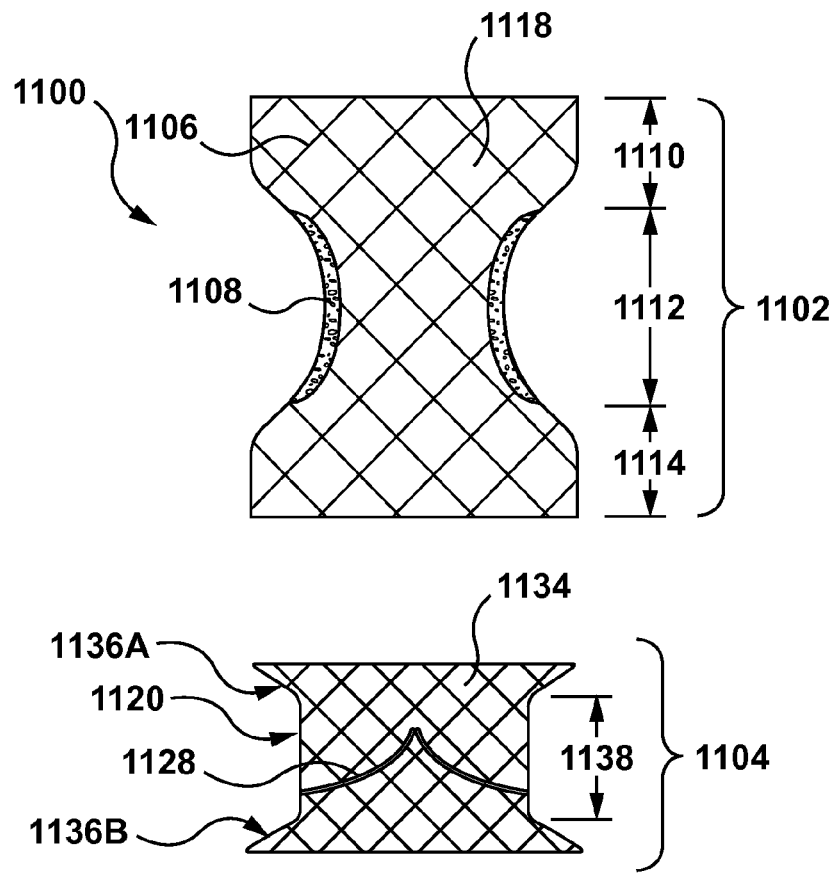
FIG. 11 is an exploded view of a valve prosthesis system according to another embodiment hereof, wherein the valve prosthesis system includes a docking component and a prosthetic valve component that couple together via mating configurations, the docking component and the prosthetic valve component each being shown in an expanded configuration.
Figure 12:
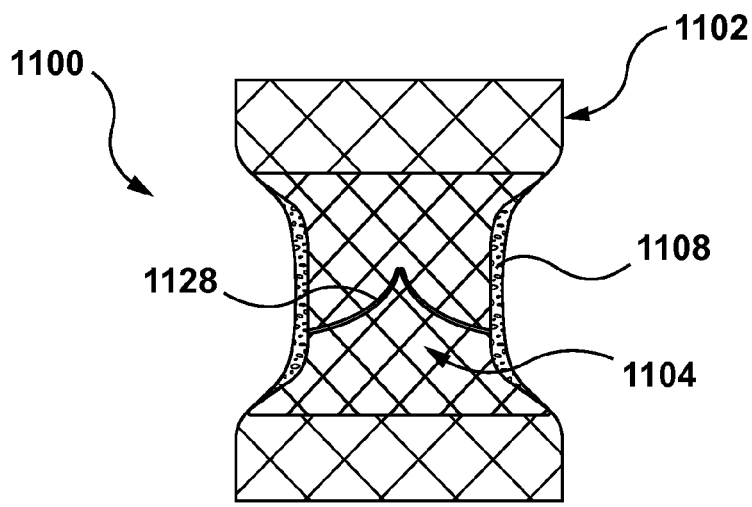
FIG. 12 is a side view of the valve prosthesis system of FIG. 11, wherein the prosthetic valve component is disposed within the docking component.

FIG. 11 and FIG. 12 illustrate a valve prosthesis system 1100 according to another embodiment hereof in which a docking component 1102 and a prosthetic valve component 1104 thereof couple together via mating configurations or profiles. FIG. 11 is an exploded side view of valve prosthesis system 1100, while FIG. 12 is a side view of prosthetic valve component 1104 being disposed or deployed within docking component 1102. Docking component 102 includes a tubular scaffold 1106 having diamond-shaped openings 1118 which may be formed by a laser-cut manufacturing method and/or another conventional stent/scaffold forming method as would be understood by one of ordinary skill in the art. Tubular scaffold 1106 includes a proximal or end portion 1110, a distal or end portion 1114, and an intermediate waist portion 1112 disposed between proximal and distal portions 1110, 1114. Intermediate waist portion 1112 has a diameter that is less than the diameters of each of proximal and distal portions 1110, 1114. A tubular skirt 1108 is disposed within and secured to the inner surface of intermediate waist portion 1112 of tubular scaffold 1106.

Prosthetic valve component 1104 includes a plurality of leaflets 1128 disposed within and secured to a tubular scaffold 1120 formed from a self-expanding material, the tubular scaffold defining diamond-shaped openings 1134 which may be formed by a laser-cut manufacturing method and/or another conventional stent/scaffold forming method as would be understood by one of ordinary skill in the art. Tubular scaffold 1120 includes a proximal end 1136A, a distal end 1136B, and a body 1138 that is disposed or extends between proximal and distal ends 1136A, 1136B. Proximal and distal ends 1136A, 1136B are flared such that body 1138 has a diameter that is less than the diameters of each of proximal and distal ends 1136A, 1136B.

Prosthetic valve component 1104 is configured to be delivered separately from docking component 1102 and is configured to couple to intermediate waist portion 1112 of docking component 1102 in situ such that tubular skirt 1108 is radially disposed around and contacts body 1138 of prosthetic valve component 1104 as shown in FIG. 12. Intermediate waist portion 1112 of tubular scaffold 1106 of docking component 1102 is configured to be longitudinally disposed between flared proximal and distal ends 1136A, 1136B of tubular scaffold 1120 of prosthetic valve component 1104 in order to couple the docking component and prosthetic valve component together in situ. Flared proximal and distal ends 1136A, 1136B of tubular scaffold 1120 provide interference with respect to intermediate waist portion 1112 of docking component 1102 and secure prosthetic valve component 1102 in place and prevent migrations due to anatomical and blood flow loads. Stated another way, an outer profile of prosthetic valve component 1104 is configured to mate with an inner profile of docking component 1102 in order to couple to the docking component and prosthetic valve component together in situ such that tubular skirt 1108 is radially disposed or sandwiched there-between. In this embodiment, tubular skirt 1108 serves as a landing or target zone for deployment of prosthetic valve component 1104. In addition, when tubular skirt 1108 is radially disposed around prosthetic valve component 1104 after deployment of the prosthetic valve component, tubular skirt 1108 prevents paravalvular leakage (PVL) by functioning to occlude or fill gaps between the perimeter of prosthetic valve component 1104 and the native valve annulus, thereby reducing, minimizing, or eliminating leaks there-between.

Figure 13:
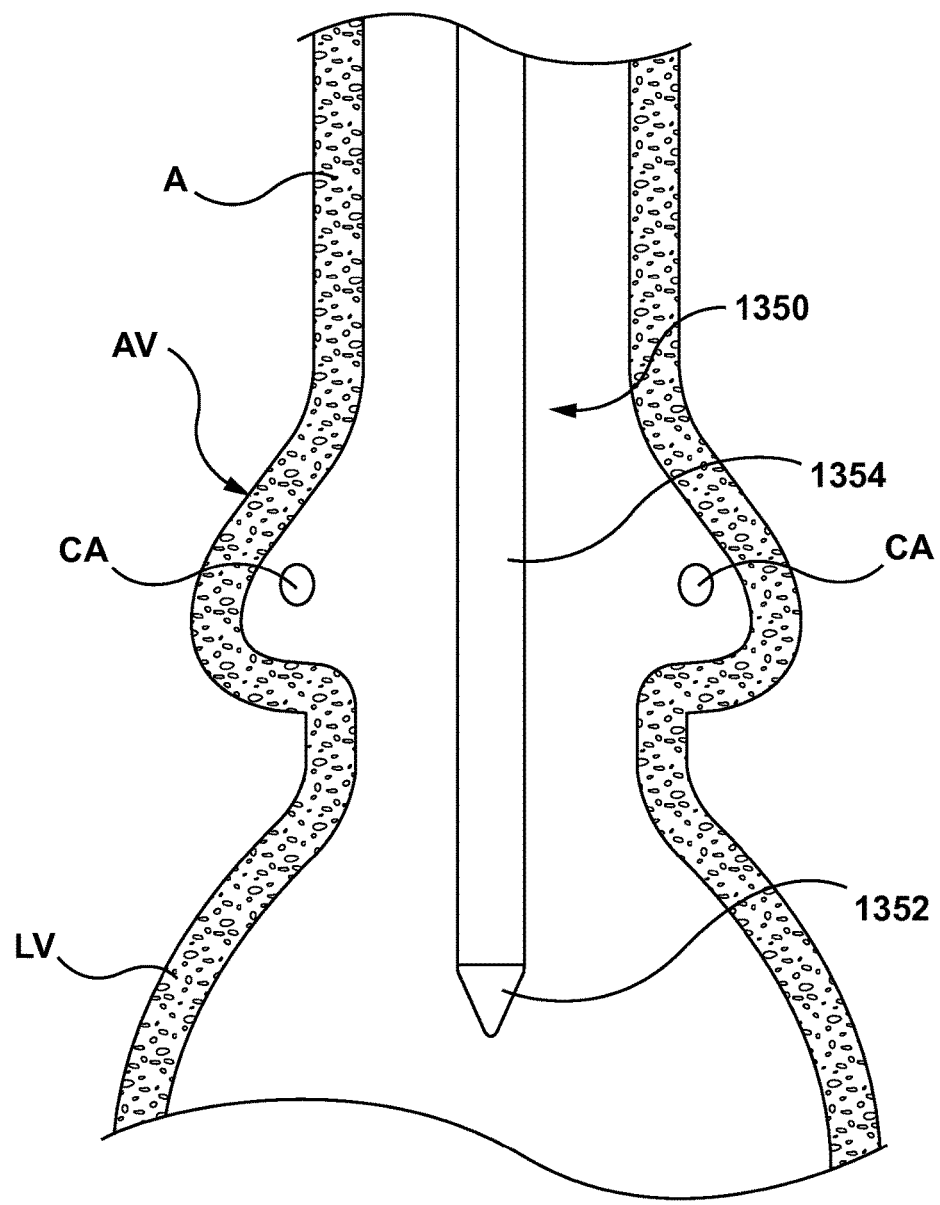
FIG. 13 depicts a step of a method for implanting the valve prosthesis of FIG. 1, wherein a catheter having the docking component mounted thereon in a compressed configuration is advanced to a native aortic valve treatment site.

FIGS. 13-17 illustrate an exemplary method of implanting the above-described valve prosthesis system 100 within a native valve according to an embodiment hereof. As will be understood by one of ordinary skill in the art, docking component 102 of valve prosthesis system 100 in a radially compressed configuration is loaded onto a distal portion of a catheter 1350. The radially compressed configuration of docking component 102 of valve prosthesis system 100 is suitable for percutaneous delivery within a vasculature. Catheter 1350 is configured for percutaneous transcatheter valve replacement, and may be one of, but is not limited to, the delivery systems described in U.S. Patent Publication No. 2011/0245917 to Savage et al., U.S. Patent Publication No. 2011/0251675 to Dwork, U.S. Patent Publication No. 2011/0251681 to Shipley et al., U.S. Patent Publication No. 2011/0251682 to Murray, III et al., and U.S. Patent Publication No. 2011/0264202 to Murray, III et al., each of which is herein incorporated by reference in its entirety. As shown in FIG. 13, in accordance with techniques known in the field of interventional cardiology and/or interventional radiology, catheter 1350 having distal end 1352 is transluminally advanced in a retrograde approach through the vasculature to the treatment site, which in this instance is a target diseased native aortic valve AV that extends between a patient's left ventricle LV and a patient's aorta A. The coronary arteries $C_A$ are also shown on the sectional view of FIG. 13. Delivery of catheter 1350 to the native aortic valve AV may be accomplished via a percutaneous transfemoral approach or may be positioned within the desired area of the heart via different delivery methods known in the art for accessing heart valves. During delivery, docking component 102 of valve prosthesis system 100 remains compressed within an outer sheath 1354 of catheter 1350. Catheter 1350 is advanced until distal end 1352 is distal to the native aortic valve AV and disposed within the left ventricle LV as shown in FIG. 13. In an embodiment, catheter 1350 is advanced approximately 5 mm into the left ventricle LV.

Figure 14:
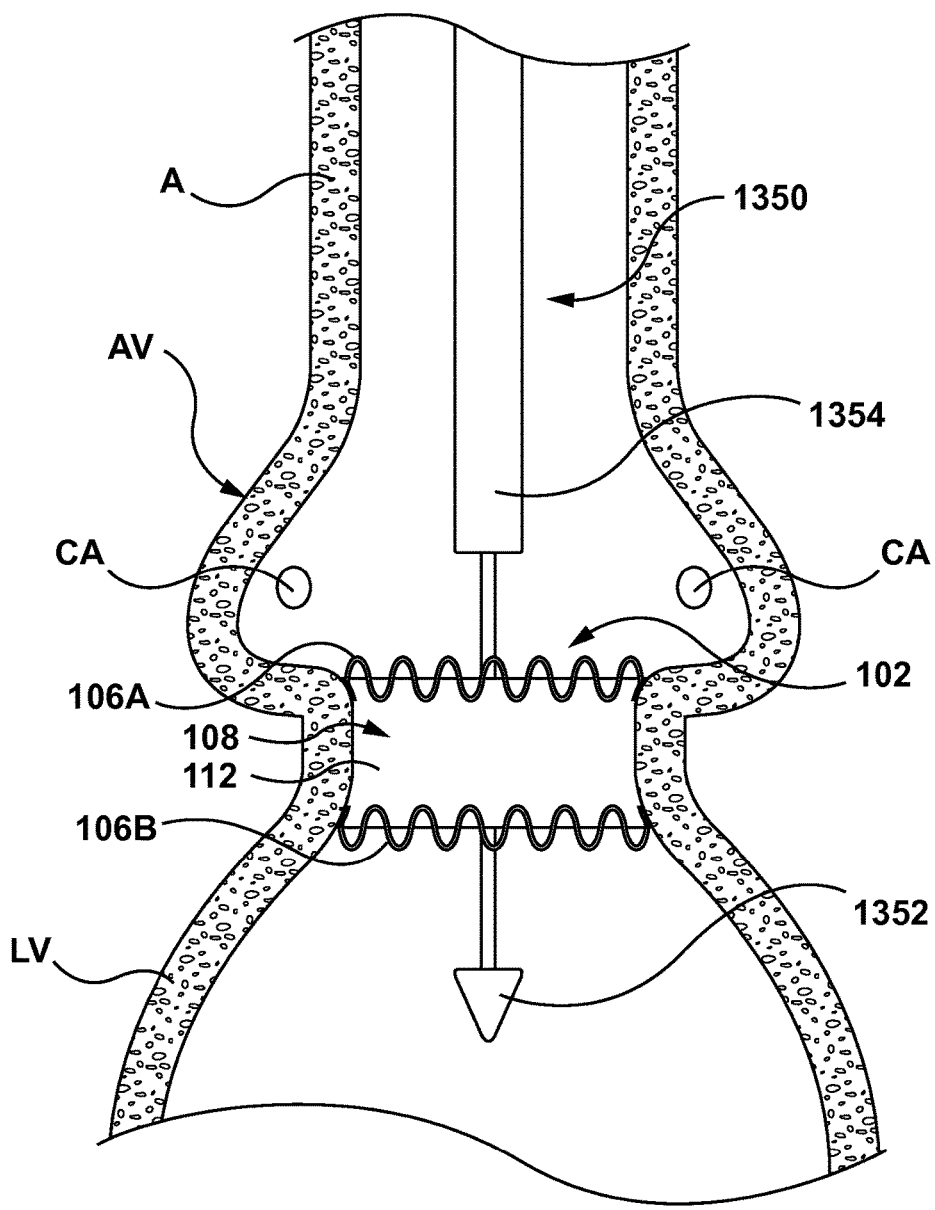
FIG. 14 depicts another step of a method for implanting the valve prosthesis of FIG. 1, wherein an outer sheath of the catheter is retracted to release the docking component of the valve prosthesis system.

Once catheter 1350 is positioned as desired, outer sheath 1354 of catheter 1350 is retracted to release docking component 102 of valve prosthesis system 100. Docking component 102 is then deployed to its expanded configuration within the native heart valve as shown in FIG. 14. When deploying docking component 102, it may be desirable to apply tension to intermediate portion 112 of tubular skirt 108 of docking component 102. More particularly, outer sheath 1354 of catheter 1350 may be retracted to expose only second annular scaffold 106B and at least a portion of intermediate portion 112 of tubular skirt 108 of docking component 102. Once released from outer sheath 1354, self-expanding second annular scaffold 106B returns to its expanded or deployed configuration. Upon release from outer sheath 1354, intermediate portion 112 of tubular skirt 108 of docking component 102 may include slack in which the material thereof is baggy, saggy, or otherwise loose. Slack may be present since intermediate portion 112 is not supported by any tubular or circumferential scaffold elements. At this point in the procedure, first annular scaffold 106A is still restrained within outer sheath 1354 but second annular scaffold 106B is deployed against the annulus of the native aortic valve AV. The entire catheter 1350 having docking component 102 mounted thereon may be pulled or proximally retracted by the user, or the catheter may include a separate mechanism (not shown) such that docking component 102 may be separately or independently pulled or proximally retracted without retracting the entire catheter 1350. With second annular scaffold 106B seated in apposition with the annulus of native aortic valve AV, catheter 1350 is proximally retracted in order to supply tension to intermediate portion 112 of tubular skirt 108. Catheter 1350 is pulled proximally until intermediate portion 112 of tubular skirt 108 is taut or stretched to a generally straight configuration and no slack is present along the length of intermediate portion 112. During the step of applying tension to tubular skirt 108, deployment of docking component 102 would preferably be monitored through imaging (e.g. fluoro, angio) to ensure that second annular scaffold 106B does not migrate but rather remains seated in apposition with the annulus of native aortic valve AV.

Once tension has been applied to tubular skirt 108 if desired, i.e., after intermediate portion 112 of tubular skirt 108 is taut, outer sheath 1354 of catheter 1350 is retracted to expose first annular scaffold 106A. Once released from outer sheath 1354, self-expanding first annular scaffold 106A returns to its expanded or deployed configuration and deploys against the annulus of native aortic valve AV, thereby anchoring valve prosthesis system 100 to the aortic wall. Both first and second annular scaffolds 106A, 106B are deployed against the annulus of native aortic valve AV such that tubular skirt 108 does not cover or extend over the sinus proximal to the annulus of native aortic valve AV. Catheter 1350 is then removed and docking component 102 remains deployed within the native aortic valve AV. If the native aortic valve AV includes native valve leaflets (not shown in FIGS. 14-18) and such leaflets have not been removed or excised, docking component 102 is deployed within the native valve leaflets of the patient's defective valve, retaining the native valve leaflets in a permanently open state.

Figure 15:
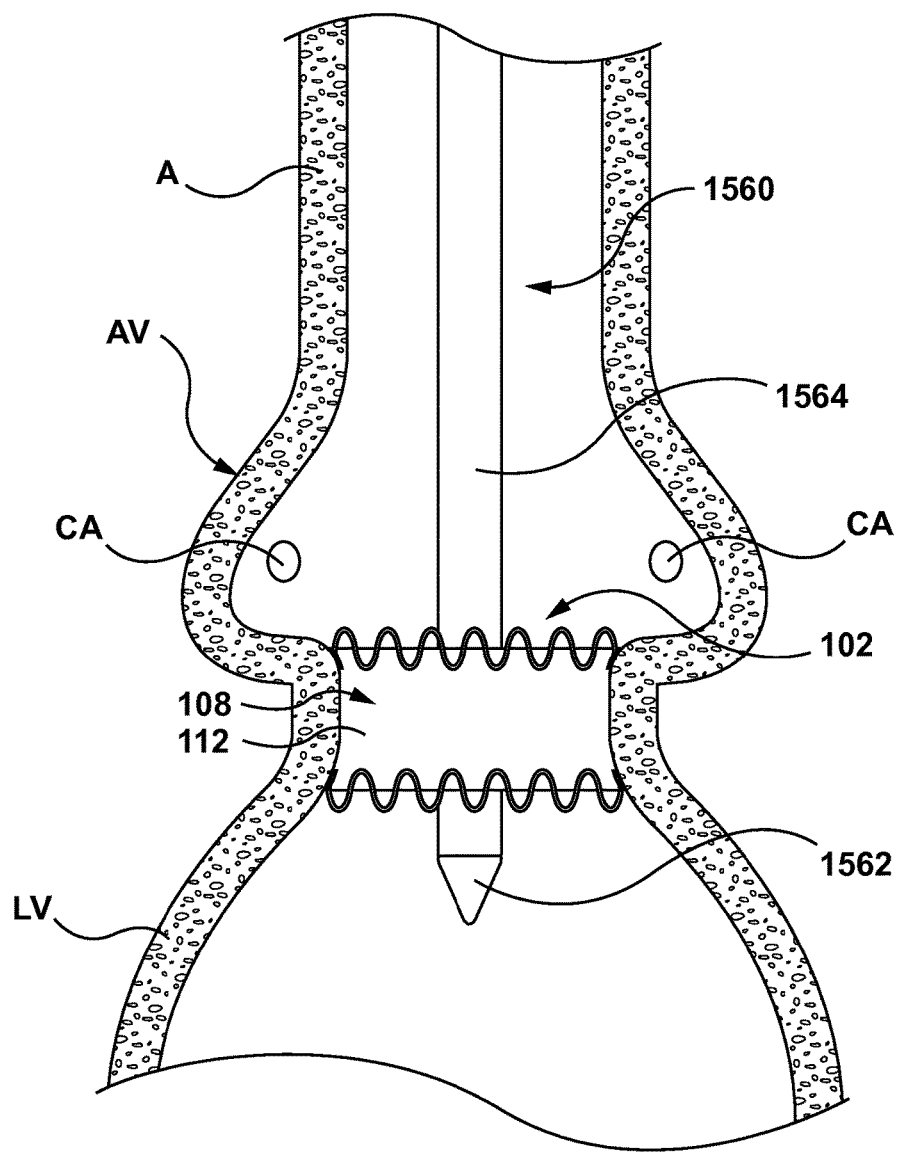
FIG. 15 depicts another step of a method for implanting the valve prosthesis of FIG. 1, wherein a second catheter having the prosthetic valve component mounted thereon in a compressed configuration is advanced to a native aortic valve treatment site and through the deployed docking component.

After deployment of docking component 102, prosthetic valve component 104 of valve prosthesis system 100 in a radially compressed configuration is loaded onto a distal portion of a catheter 1560. The radially compressed configuration of prosthetic valve component 104 of valve prosthesis system 100 is suitable for percutaneous delivery within a vasculature. Catheter 1560 is configured for percutaneous transcatheter valve replacement, and may be one of, but is not limited to, the delivery systems described in U.S. Patent Publication No. 2011/0245917 to Savage et al., U.S. Patent Publication No. 2011/0251675 to Dwork, U.S. Patent Publication No. 2011/0251681 to Shipley et al., U.S. Patent Publication No. 2011/0251682 to Murray, III et al., and U.S. Patent Publication No. 2011/0264202 to Murray, III et al., each of which is herein incorporated by reference in its entirety. As shown in FIG. 15, in accordance with techniques known in the field of interventional cardiology and/or interventional radiology, catheter 1560 having distal end 1562 is transluminally advanced in a retrograde approach through the vasculature to the deployed docking component 102. Delivery of catheter 1560 to the native aortic valve AV may be accomplished via a percutaneous transfemoral approach or may be positioned within the desired area of the heart via different delivery methods known in the art for accessing heart valves. During delivery, prosthetic valve component 104 of valve prosthesis system 100 remains compressed within an outer sheath 1564 of catheter 1560. Catheter 1560 is advanced until distal end 1562 is advanced through the deployed docking component 102 and is distal to the native aortic valve AV and disposed within the left ventricle LV as shown in FIG. 15.

As previously described, intermediate portion 112 of tubular skirt 108 of the deployed docking component serves as a landing or target zone for prosthetic valve component 104. Once catheter 1560 is positioned as desired, i.e., with prosthetic valve component 104 adjacent to intermediate portion 112 of tubular skirt 108 of the deployed docking component, outer sheath 1564 of catheter 1560 is retracted to release prosthetic valve component 104 of valve prosthesis system 100. Prosthetic valve component 104 is then deployed to its expanded configuration within intermediate portion 112 of tubular skirt 108 of the deployed docking component. Deployment of prosthetic valve component 104 occurs after deployment of docking component 102. When deploying prosthetic valve component 104, it may be desirable to embed barbs 132 (if present) into intermediate portion 112 of tubular skirt 108. More particularly, the step of deploying prosthetic valve component 104 to the expanded configuration within intermediate portion 112 of the deployed docking component includes deploying prosthetic valve component 104 to a partially deployed configuration. When in the partially deployed configuration, catheter 1564 and prosthetic valve component 104 mounted thereon are rotated as shown in FIG. 16 via directional arrow 1670 in order to embed barbs 132 into intermediate portion 112 of the deployed docking component and thereby couple prosthetic valve component 104 to docking component 102 in situ.

Figure 16:
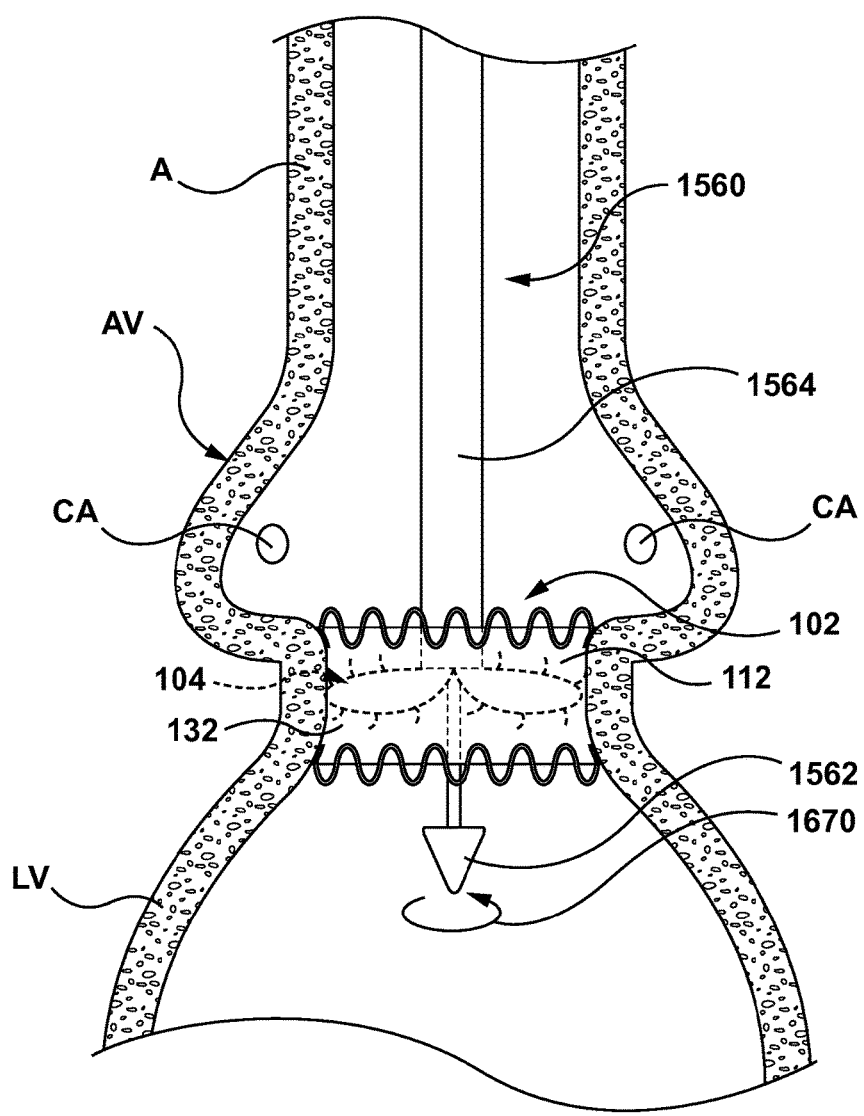
FIG. 16 depicts another step of a method for implanting the valve prosthesis of FIG. 1, wherein an outer sheath of the second catheter is retracted to partially release the prosthetic valve component and the prosthetic valve component is rotated in order to embed barbs of the prosthetic valve component into the skirt of the docking component.
Figure 16A:
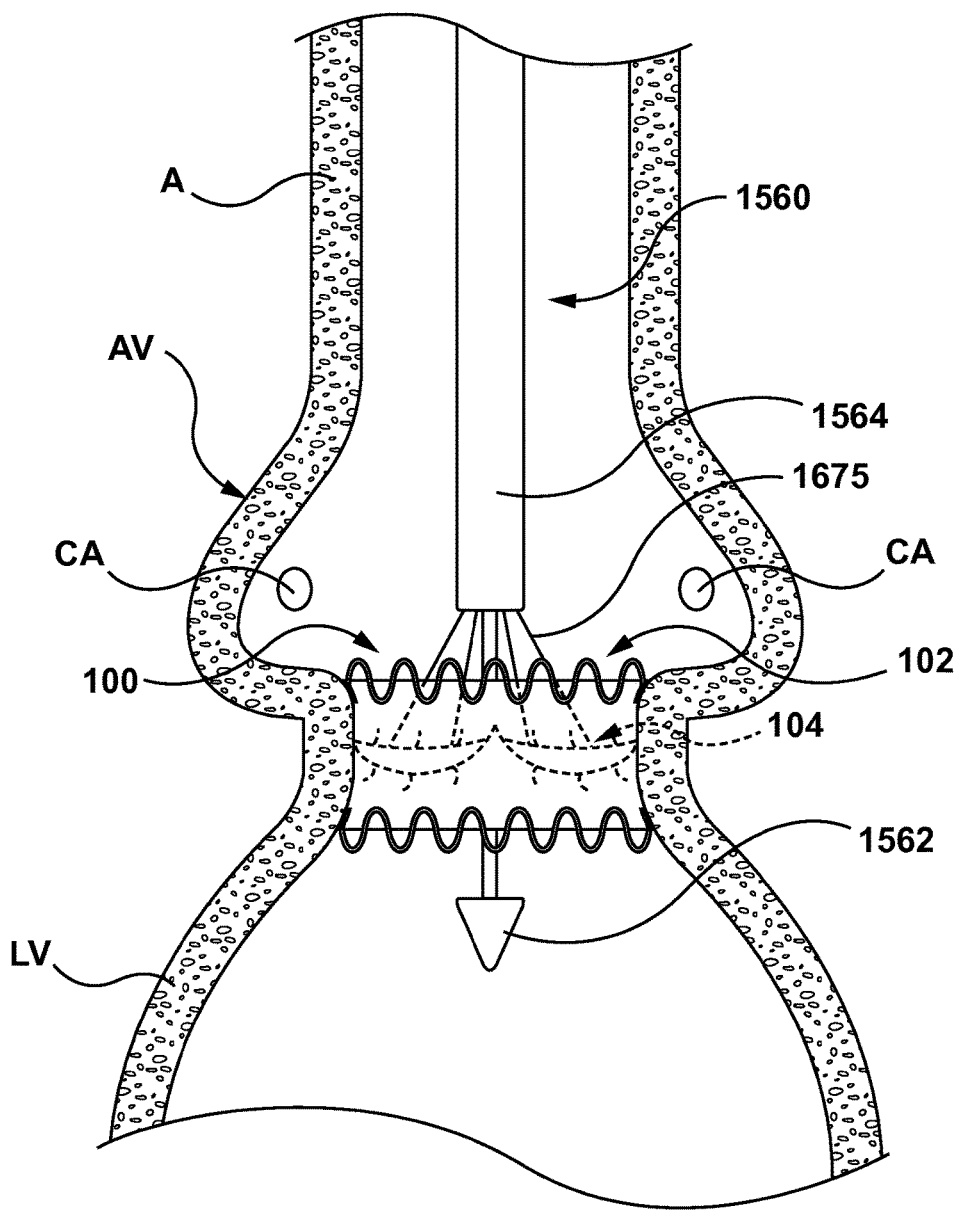
FIG. 16A depicts another step of a method for implanting the valve prosthesis of FIG. 1 according to an alternative embodiment hereof, wherein rods extend between the proximal end of the prosthetic valve component as a means to rotate the prosthetic valve component in order to embed barbs of the prosthetic valve component into the skirt of the docking component.
Figure 17:
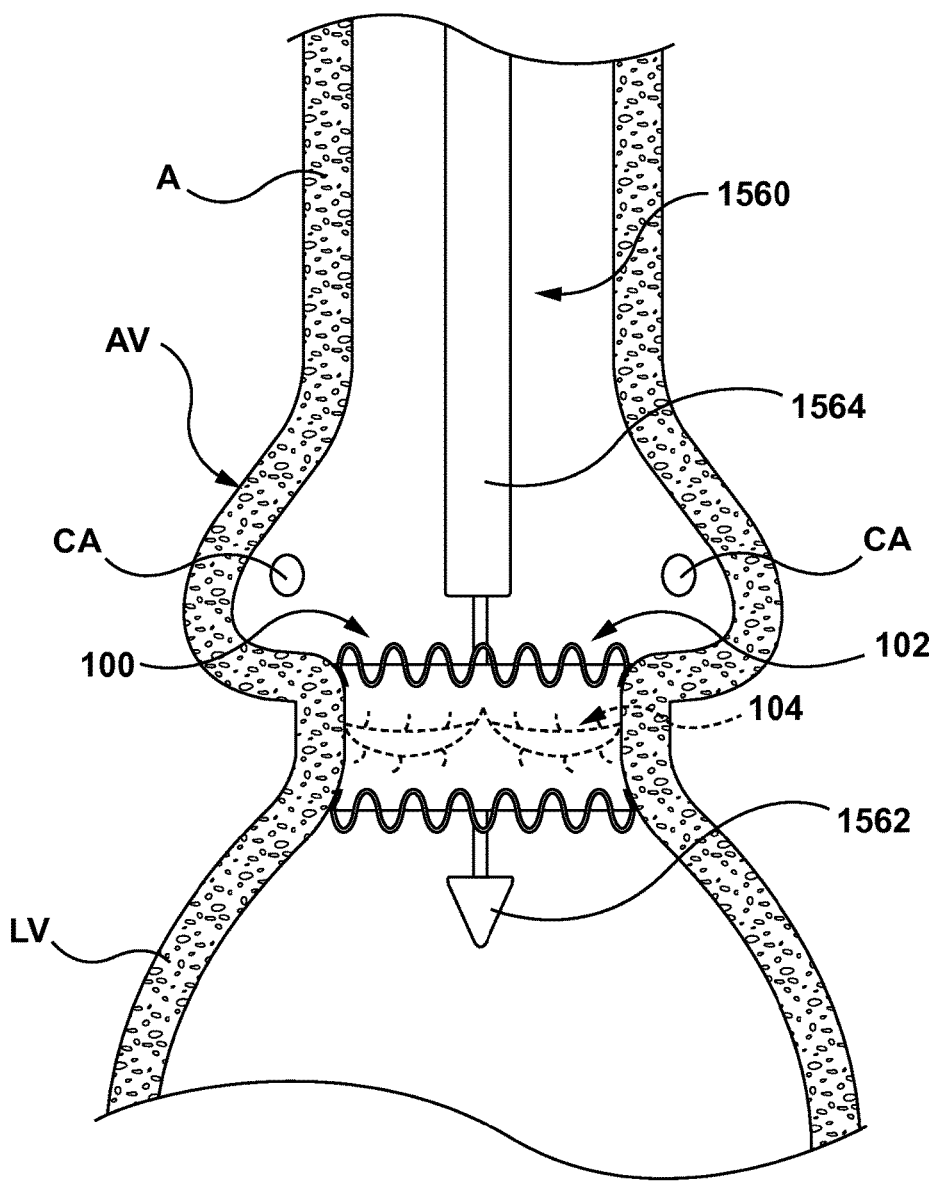
FIG. 17 depicts another step of a method for implanting the valve prosthesis of FIG. 1, wherein the outer sheath of the second catheter has been retracted to fully release the prosthetic valve component and the prosthetic valve component and the docking component are deployed in the native aortic valve treatment site.

In an embodiment depicted in FIG. 16, prosthetic valve component 104 is deployed to a partially deployed configuration by restraining only a proximal end or portion of scaffold 120 within outer sheath 1564 of catheter 1560. Stated another way, a distal end of portion of scaffold 120 is deployed to initiate contact with intermediate portion 112 of the deployed docking component while the proximal engagement of scaffold 120 with catheter 1560 allows rotation to be applied at the proximal end of the catheter. In another embodiment hereof depicted in FIG. 16A, prosthetic valve component 104 may be fully deployed while a connection is maintained between catheter 1560 and fully deployed prosthetic valve component 104 in order to transfer rotation of catheter 1560 to fully deployed prosthetic valve component 104. For example, rods 1675 or similar structures may extend between catheter 1560 and fully deployed prosthetic valve component 104 in order to connect the proximal end of prosthetic valve component 104 to catheter 1560. Rods 1675 would be circumferentially stiff, thus allowing sufficient rotational force to be applied to engage barbs 132 with intermediate portion 112 of the deployed docking component. Rods 1675 may be wider in the circumferential direction and thinner in the radial direction so as to flexible enough to be retracted and sheathed into catheter 1560 after barbs 132 are embedded as desired. Rods 1675 extend through outer sheath 1564 of catheter 1560 such that the proximal ends thereof (not shown) are coupled to a handle mechanism (not shown) of catheter 1560 for control thereof. Rods 1675 are disengaged from the proximal end of prosthetic valve component 104 following valve deployment. For example, in an embodiment, rods 1675 may be disengaged from the proximal end of prosthetic valve component 104 following valve deployment by applying a twisting motion to catheter 1560. After prosthetic valve component 104 is secured to docking component 102 via embedded barbs 132, additional twisting motion applied to rods 1675 functions to break the joints or connections between the distal ends of rods 1675 and the proximal end of prosthetic valve component 104.

After prosthetic valve component 104 is coupled to docking component 102 via barbs 132, outer sheath 1564 of catheter 1560 is further retracted to fully deploy and release prosthetic valve component 104 of valve prosthesis system 100. Stated another way, prosthetic valve component 104 is deployed to its fully expanded or deployed configuration within intermediate portion 112 of the deployed docking component as shown on FIG. 17. After deployment, intermediate portion 112 of tubular skirt 108 serves to prevent paravalvular leakage (PVL) as described herein.

Although the above-described method of implanting valve prosthesis system 100 utilized two separate catheters, i.e., catheter 1350 for delivering docking component 102 and catheter 1560 for delivering prosthetic valve component 104, in another embodiment hereof a single catheter may be utilized for implanting valve prosthesis system 100. More particularly, a single catheter or delivery system may be modified to deliver valve prosthesis system 100 in a two-stage deployment in which docking component 102 and prosthetic valve component 104 are concurrently delivered or advanced to the target native valve or treatment site but docking component 102 is deployed prior to prosthetic valve component 104. Stated another way, even if concurrently delivered on a single catheter or delivery system, prosthetic valve component 104 is configured to be deployed after or subsequent to deployment of docking component 102.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A valve prosthesis system comprising:
   a docking component having a compressed configuration for percutaneous delivery within a vasculature and an expanded configuration for deployment within a native heart valve, the docking component comprising,
      a tubular body formed from an impermeable material, the tubular body having opposing first and second end portions and an intermediate portion extending between the first and second end portions,
      a first annular scaffold attached to the tubular body along the first end portion thereof, and
      a second annular scaffold attached to the tubular body along the second end portion thereof, wherein the first and second annular scaffolds are independent from each other, wherein the intermediate portion of the tubular body is unsupported such that neither of the first or second annular scaffolds surround the intermediate portion of the tubular body; and a prosthetic valve component having a compressed configuration for percutaneous delivery within a vasculature and an expanded configuration for deployment within the intermediate portion of the docking component, wherein the prosthetic valve component is configured to be delivered separately from the docking component and includes barbs that are configured to embed into the intermediate portion of the tubular body of the docking component to couple the prosthetic valve component to the intermediate portion in situ without contacting the first and second annular scaffolds of the docking component.

2. The valve prosthesis system of claim 1, wherein the first and second annular scaffolds are sized to anchor the valve prosthesis system against native valve tissue when the docking component is in the expanded configuration.

3. The valve prosthesis system of claim 1, wherein the prosthetic valve component includes a scaffold and at least two leaflets.

4. The valve prosthesis system of claim 3, wherein the prosthetic valve component includes three leaflets and the scaffold is an annular ring that defines three posts aligned with commissures of the three leaflets of the prosthetic valve component.

5. The valve prosthesis system of claim 4, wherein the annular ring includes the barbs on an outside surface thereof.

6. The valve prosthesis system of claim 1, wherein the first and second annular scaffolds extend beyond the first and second end portions of the tubular body.

7. The valve prosthesis system of claim 1, wherein the impermeable material is selected from a group consisting of a polymer material, a fabric material, or a pericardium.

8. A valve prosthesis system, the system comprising:
an exterior docking component including a tubular skirt, a first annular scaffold attached to a first end of the tubular skirt, and a second annular scaffold attached to a second end of the tubular skirt, the exterior docking component having a compressed configuration for percutaneous delivery within a vasculature and an expanded configuration for deployment within a native heart valve, wherein the first and second annular scaffolds are independent from each other and an intermediate portion of the tubular skirt that longitudinally extends between the first and second annular scaffolds is unsupported such that neither of the first or second annular scaffolds surround the intermediate portion of the tubular skirt; and
an interior dockable component including a scaffold and at least two valve leaflets disposed within and secured to the scaffold, the interior dockable component having a compressed configuration for percutaneous delivery within a vasculature and an expanded configuration for deployment within the tubular skirt of the exterior docking component, wherein the interior dockable component includes three valve leaflets and wherein the scaffold of the interior dockable component is an annular ring that defines three posts aligned with commissures of the three valve leaflets, and
wherein the interior dockable component is configured to be delivered separately from the exterior docking component and the interior dockable component is configured to couple to the intermediate portion of the tubular skirt of the exterior docking component without contacting the first and second annular scaffolds of the exterior docking component in situ such that the tubular skirt is radially disposed around and contacts the interior dockable component.

9. The valve prosthesis system of claim 8, wherein the first and second annular scaffolds are sized to anchor the valve prosthesis system against native valve tissue when the exterior docking component is in the expanded configuration.

10. The valve prosthesis system of claim 8, wherein the annular ring includes barbs on an outside surface thereof, the barbs being configured to embed into the intermediate portion of the tubular skirt of the exterior docking component in order to couple the interior dockable component to the exterior docking component in situ.

11. The valve prosthesis system of claim 8, wherein the tubular skirt is formed from an impermeable material and the impermeable material is selected from a group consisting of a polymer material, a fabric material, or a pericardium.

12. A valve prosthesis system, the system comprising:
an exterior docking component including a tubular skirt, a first annular scaffold attached to a first end of the tubular skirt, and a second annular scaffold attached to a second end of the tubular skirt, the exterior docking component having a compressed configuration for percutaneous delivery within a vasculature and an expanded configuration for deployment within a native heart valve, wherein the first and second annular scaffolds are independent from each other and an intermediate portion of the tubular skirt that longitudinally extends between the first and second annular scaffolds is unsupported such that neither of the first or second annular scaffolds surround the intermediate portion of the tubular skirt; and
an interior dockable component including a scaffold, at least two valve leaflets disposed within and secured to the scaffold, and barbs on an outside surface thereof, the interior dockable component having a compressed configuration for percutaneous delivery within a vasculature and an expanded configuration for deployment within the skirt of the exterior docking component,
wherein the interior dockable component is configured to be delivered separately from the exterior docking component and the barbs of the interior dockable component are configured to embed into the tubular skirt of the exterior docking component in order to couple the interior dockable component to the intermediate portion of the tubular skirt of the exterior docking component in situ such that the tubular skirt is radially disposed around and contacts the interior dockable component.

13. The valve prosthesis system of claim 12, wherein the interior dockable component includes three valve leaflets and wherein the scaffold of the interior dockable component is an annular ring that defines three posts aligned with commissures of the three valve leaflets.

14. The valve prosthesis system of claim 12, wherein the first and second annular scaffolds each include a sinusoidal patterned ring sized to anchor the valve prosthesis system against native valve tissue when the exterior docking component is in the expanded configuration.

15. The valve prosthesis system of claim 12, wherein the intermediate portion of the tubular skirt has a longitudinal length at least as long as the interior dockable component.

16. The valve prosthesis system of claim 1, wherein each of the first annular scaffold and the second annular scaffold is a sinusoidal patterned ring.

17. The valve prosthesis system of claim 1, wherein the intermediate portion of the tubular body has a longitudinal length at least as long as the prosthetic valve component.

18. The valve prosthesis system of claim 8, wherein each of the first annular scaffold and the second annular scaffold is a sinusoidal patterned ring.

19. The valve prosthesis system of claim 8, wherein the intermediate portion of the tubular skirt has a longitudinal length at least as long as the interior dockable component.

* * * * *